(12) United States Patent
Baker

(10) Patent No.: US 7,248,922 B2
(45) Date of Patent: *Jul. 24, 2007

(54) TIMING REFRACTORY PERIOD FOR CARDIAC RESYNCHRONIZATION PACING

(75) Inventor: Kenneth L. Baker, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 579 days.

This patent is subject to a terminal disclaimer.

(21) Appl. No.: 10/794,169

(22) Filed: Mar. 5, 2004

(65) Prior Publication Data

US 2004/0243189 A1    Dec. 2, 2004

Related U.S. Application Data

(63) Continuation of application No. 09/852,125, filed on May 9, 2001, now Pat. No. 6,704,599.

(51) Int. Cl.
*A61N 1/365* (2006.01)
(52) U.S. Cl. ........................................ 607/14
(58) Field of Classification Search .............. 607/4, 607/9, 11, 13–15, 17–26
See application file for complete search history.

(56) References Cited

U.S. PATENT DOCUMENTS

| | | | |
|---|---|---|---|
| 4,354,497 A | 10/1982 | Kahn | 128/419 |
| 4,928,688 A | 5/1990 | Mower | 128/419 PG |
| 5,156,149 A | 10/1992 | Hudrlik | 128/419 PG |
| 5,174,289 A | 12/1992 | Cohen | 128/419 |
| 5,233,985 A | 8/1993 | Hudrlik | 607/27 |
| 5,267,560 A | 12/1993 | Cohen | 607/25 |
| 5,370,665 A | 12/1994 | Hudrlik | 607/9 |
| 5,514,161 A | 5/1996 | Limousin | 607/9 |
| 5,584,867 A | 12/1996 | Limousin et al. | 607/9 |
| 5,674,259 A | 10/1997 | Gray | 607/20 |
| 5,797,970 A | 8/1998 | Pouvreau | 607/9 |
| 5,935,160 A | 8/1999 | Auricchio et al. | 607/122 |
| 6,496,730 B1 * | 12/2002 | Kleckner et al. | 607/9 |
| 6,704,599 B2 * | 3/2004 | Baker | 607/14 |
| 2001/0034539 A1 | 10/2001 | Stadler et al. | 607/14 |

* cited by examiner

*Primary Examiner*—George R. Evanisko
(74) *Attorney, Agent, or Firm*—Schwegman, Lundberg, Woessner & Kluth, P.A.

(57) ABSTRACT

A device and method for cardiac rhythm management in which a heart chamber is paced in accordance with a pacing mode that employs sense signals from the opposite chamber. A sensing refractory period is provided in order to prevent the pacing interval from being lengthened due to delays in conduction of excitation from the paced chamber to the sensed chamber.

20 Claims, 3 Drawing Sheets

TIMING REFRACTORY PERIOD FOR CARDIAC RESYNCHRONIZATION PACING

CROSS-REFERENCE TO RELATED APPLICATION(S)

This application is a continuation of U.S. patent application Ser. No. 09/852,125, filed on May 9, 2001 now U.S. Pat. No. 6,704,599 the specification of which is incorporated herein by reference.

FIELD OF THE INVENTION

This invention pertains to methods and apparatus for cardiac rhythm management. In particular, the invention relates to methods and apparatus for providing cardiac resynchronization pacing.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Patients with conventional pacemakers can also have compromised cardiac output because artificial pacing with an electrode fixed into an area of the myocardium does not take advantage of the above-described specialized conduction system. The spread of excitation from a single pacing site must proceed only via the much slower conducting muscle fibers of either the atria or the ventricles, resulting in the part of the myocardium stimulated by the pacing electrode contracting well before parts of the chamber located more distally to the electrode, including the myocardium of the chamber contralateral to the pacing site. Although the pumping efficiency of the heart is somewhat reduced from the optimum, most patients can still maintain more than adequate cardiac output with artificial pacing.

Heart failure is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium as described above. The resulting diminishment in cardiac output may be significant in a CHF patient whose cardiac output is already compromised. Intraventricular and/or interventricular conduction defects are also commonly found in CHF patients. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

SUMMARY OF THE INVENTION

Cardiac resynchronization therapy can most conveniently be delivered by a cardiac rhythm management device in accordance with a bradycardia pacing mode so that the activation patterns between and within selected heart chambers are both resynchronized and paced concurrently. One way to implement resynchronization therapy is to designate one heart chamber as the rate chamber and the contralateral chamber as the synchronized chamber and then pace one or both chambers based upon rate chamber senses. In one particular resynchronization pacing mode, only the synchronized chamber is paced in accordance with a demand pacing algorithm defined with respect to rate chamber senses. For example, if the right and left ventricles are designated as the rate and synchronization chambers, only the left ventricle is paced in accordance with a conventional bradycardia pacing mode defined with respect to right ventricular sense signals. That is, a left ventricular pace is delivered at a pacing instant that occurs upon expiration of an escape interval without receiving a right ventricular sense, where the escape interval is reset upon a right ventricular sense or after delivery of a left ventricular pace.

Pacing only the synchronized chamber in this manner means that the rate chamber will be depolarized subsequent to the delivery of the pace as excitation is conducted from the synchronized chamber to the rate chamber. Although the rate chamber sensing channel may be rendered refractory upon delivery of the pace, if the conduction time is longer than the refractory period, a rate chamber sense of the depolarization resulting from the pace will reset the escape interval. This will necessarily decrease the rate at which paces are delivered below that which is desired by lengthening the pacing interval. The present invention therefore employs a selected timing refractory period, initiated by a pace to the synchronized chamber, during which rate chamber senses are ignored for purposes of resetting the escape interval. Rate chamber senses occurring within the timing refractory period due to conduction of excitation resulting from a pace then do not affect the pacing rate but may be counted for purposes of detecting a tachyarrhythmia in the rate chamber.

DETAILED DESCRIPTION

The present invention is concerned with a method and system for delivering cardiac resynchronization pacing in a particular mode. The following is a description of the hardware used to deliver such therapy, of resynchronization pacing in general, and an exemplary embodiment of the invention.

1. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
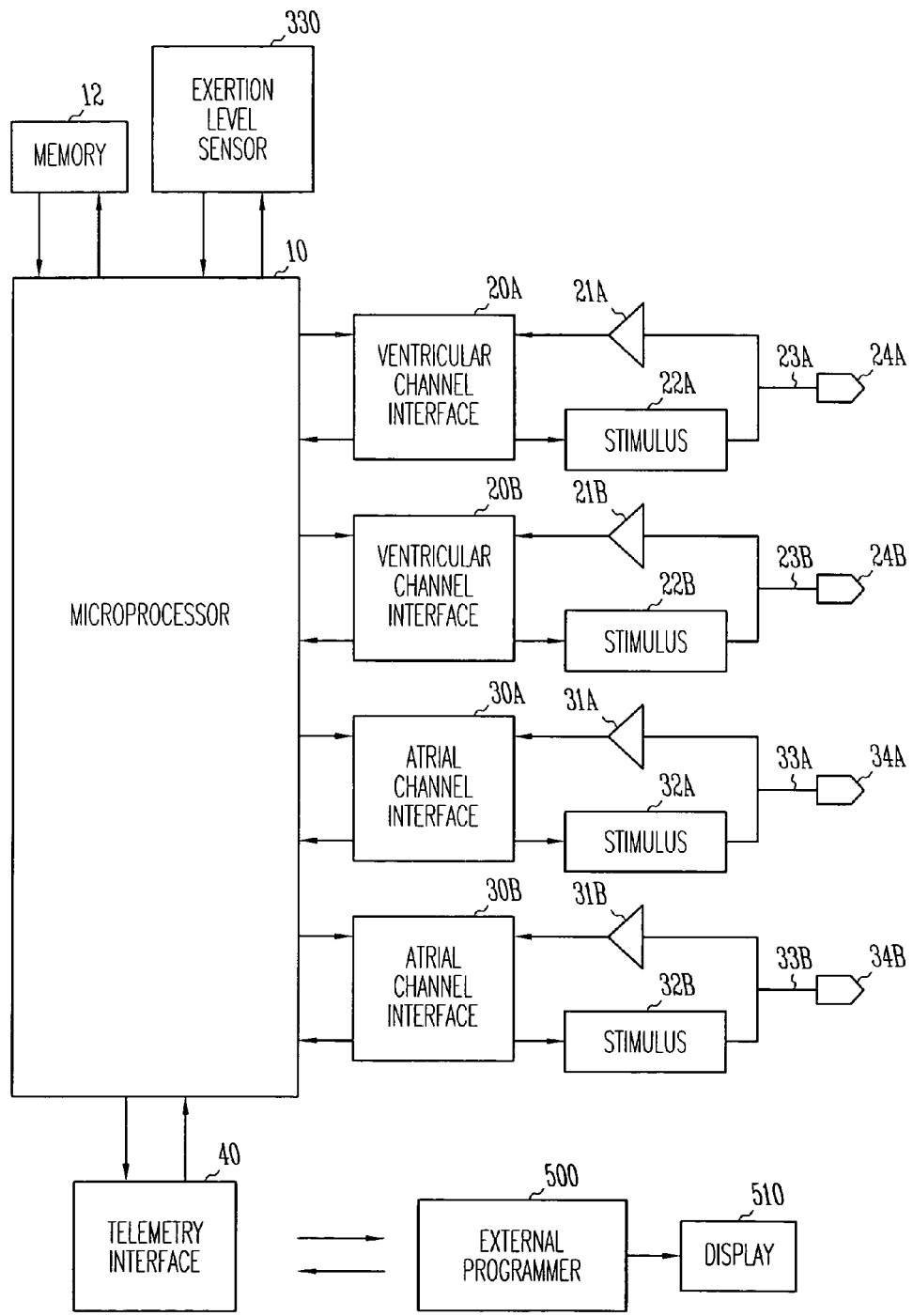
FIG. 1 is a system diagram of a pacemaker configured for resynchronization pacing.

FIG. 1 shows a system diagram of a microprocessor-based pacemaker physically configured with sensing and pacing channels for both atria and both ventricles. The controller 10 of the pacemaker is a microprocessor that communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a-b, leads 33a-b, sensing amplifiers 31a-b, pulse generators 32a-b, and atrial channel interfaces 30a-b which communicate bidirectionally with microprocessor 10. The device also has ventricular sensing and pacing channels for both ventricles comprising electrodes 24a-b, leads 23a-b, sensing amplifiers 21a-b, pulse generators 22a-b, and ventricular channel interfaces 20a-b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces 20a-b and 30a-b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, and implements timers for defining escape intervals and sensory refractory periods. Both bradycardia and anti-tachycardia pacing modes may be implemented in code executed by the controller. In the latter, paces are delivered according to a defined protocol that acts so as to terminate a tachyarrhythmia when such a rhythm is detected by the sensing channels.

2. Bradycardia Pacing Modes

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modem pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate interval is then the sum of the atrial escape interval and the atrio-ventricular interval.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be use. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing in accordance with a synchronized pacing mode as described below.

It is advantageous to deliver resynchronization therapy in conjunction with one or more synchronous bradycardia pacing modes, such as are described above. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. One heart chamber is designated as the rate chamber, and the heart chamber contralateral to the rate chamber is designated as a synchronized chamber. For example, the right ventricle may be designated as the rate ventricle with the left ventricle designated as the synchronized ventricle, and the paired atria may be similarly designated. The synchronized chamber is then paced with an inhibited demand pacing mode using an escape interval that is reset by a sense occurring in the contralateral rate chamber or a pace delivered to either chamber.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pseudo-pace the rate chamber whenever the synchronized chamber is paced before the rate chamber is paced, such that the pseudo-pace inhibits a rate chamber pace and resets any rate chamber escape intervals. Such pseudo-pacing can be combined with the offset synchronized pacing mode using a negative offset to pace the synchronized chamber before the rate chamber and thus pseudo-pace the rate chamber, which inhibits the real scheduled rate chamber pace and resets the rate chamber pacing escape intervals. Sensed events in the rate chamber will thus inhibit the synchronized chamber-only pacing, which may benefit some patients by preventing pacing that competes with intrinsic activation (i.e., fusion beats). In order to prevent pacing the synchronized chamber during its vulnerable period, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand pacing modes with or without atrial tracking. A left ventricular pace is then delivered upon expiration of the AVI escape interval or expiration of the LRL escape interval, with left ventricular pacing inhibited by a right ventricular sense that restarts the LRL escape interval and stops the AVI escape interval.

4. Timing Refractory Period

When a pace is delivered to the synchronized chamber, the pace will be received by the rate chamber sensing channel as a far-field sense unless the channel is rendered refractory. Accordingly, a cross-chamber sensing refractory period for the rate chamber sensing channel may be provided that is initiated upon delivery of a pace to the synchronized chamber. The sensing refractory period may be made up of a blanking interval, during which the sensing amplifiers are blanked and no signals are received, and/or a software implemented refractory period during which received signals are simply ignored by the device. The sensing refractory period thus prevents a far-field sense due to a pace from being counted for purposes of detecting a tachyarrhythmia.

In a synchronized chamber-only pacing mode, the depolarization resulting from a pace delivered to the synchronized chamber is conducted to the rate chamber and causes depolarization there also if the rate chamber has not been earlier depolarized by intrinsic activation (e.g., conduction of excitation from the AV node in the case of a ventricle). If the conducted depolarization is detected by the rate chamber sensing channel, the rate chamber sense will be used to reset the pacing escape interval. Since a conducted depolarization is part of the same cardiac cycle as the pace delivered to the synchronized chamber, the resetting of the escape interval effectively lengthens the pacing interval and hence lowers the pacing rate below that which is desired. The pacing interval is lengthened by the conduction time between the paced synchronized chamber and the rate chamber.

In the following example, the right and left ventricles are the rate and synchronized chambers, respectively. The pacing interval is increased by the LV-to-RV conduction time when the conducted depolarization is sensed by the RV sensing channel. The following table illustrates the effective pacing rate for conduction times of 150, 250, and 250 ms and intended pacing rates of 50, 100, and 150 ppm:

|  | LV-to-RV Conduction Time | | |
| --- | --- | --- | --- |
| Intended Rate | 150 | 250 | 350 |
| 50 | 44 | 41 | 39 |
| 100 | 80 | 71 | 63 |
| 150 | 109 | 92 | 80 |

Figure 2A:
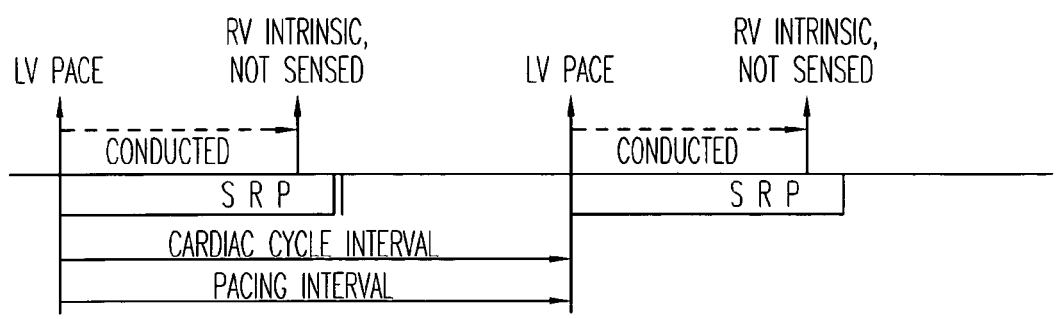
FIGS. 2A-B are timing diagrams showing right ventricular senses as a result of a conducted left ventricular pace.
Figure 2B:
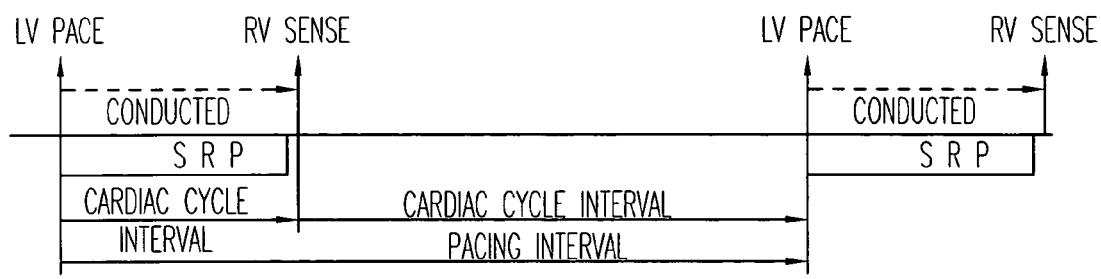

This undesirable decrease in the pacing rate can be avoided by lengthening the sensing refractory period so that conducted depolarizations fall within the period and are not sensed by the RV sensing channel. FIG. 2A illustrates this situation where an RV sense resulting from a conducted LV pace occurs within the sensing refractory period SRP and thus goes unsensed with no resetting of the escape interval. The intended pacing interval is thus unaffected. In order to ensure that ventricular tachyarrhythmias can be detected by measuring the rate at which intrinsic depolarizations occur, however, it is necessary that the sensing refractory period be no longer than one-half of the escape interval. At high pacing rates, such as may occur in rate-adaptive pacing during periods of high metabolic demand, the sensing refractory period cannot be lengthened enough to avoid sensing conducted depolarizations if the LV-to-RV conduction time is long. For example, with a pacing rate of 150 ppm, the sensing refractory period can be no longer than 200 milliseconds without compromising detection of ventricular tachyarrhythmias. FIG. 2B illustrates this situation where the RV sense from the conducted LV pace occurs outside the sensing refractory period and resets the escape interval. A new cardiac cycle is then started at the time of the RV sense that effectively lengthens the pacing interval.

Figure 3A:
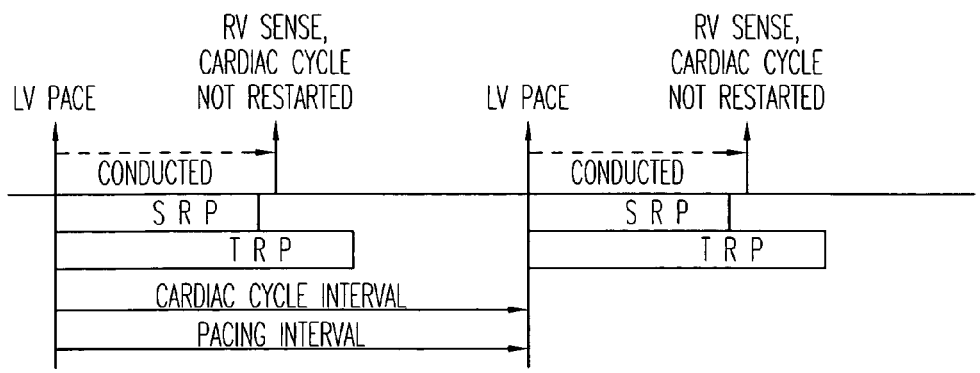
FIGS. 3A-B are timing diagrams illustrating the timing refractory period.
Figure 3B:
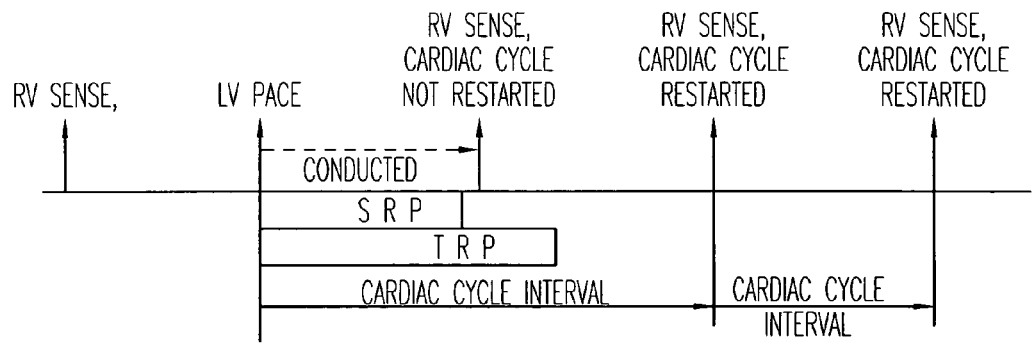

In accordance with the invention, a timing refractory period for the rate chamber sensing channel initiated by a synchronized chamber pace is implemented in order to prevent resetting of the escape interval. During this timing refractory period, senses are ignored for purposes of resetting the escape interval but counted for purposes of detecting a tachyarrhythmia. The timing refractory period can thus be as long as necessary to avoid resetting of the escape interval by senses of conducted depolarizations (e.g., the timing refractory period can be greater than one-half of the escape interval), while the sensing refractory period can be made short enough that tachyarrhythmias are detectable at all pacing rates. FIG. 3A shows the operation of the timing refractory period when no ventricular tachyarrhythmia is present. An RV sense from a conducted LV pace is shown occurring outside of the sensing refractory period SRP but within the timing refractory period TRP. There is therefore no lengthening of the pacing interval, and the presence of a ventricular tachyarrhythmia can be checked for by measuring the interval between RV senses. FIG. 3B shows the operation of the timing refractory period during a ventricular tachyarrhythmia. An RV sense from a conducted LV pace again occurs outside the sensing refractory period SRP but within the timing refractory period TRP so that no lengthening of the pacing interval occurs. Only the intervals between successive RV senses are used for detection of a ventricular tachyarrhythmia, including the two RV senses that straddle the LV pace. When a ventricular tachyarrhythmia is detected, the device controller can cease bradycardia pacing and/or initiate anti-tachycardia pacing. The former action may be implemented by discontinuing the timing refractory period to enable the RV senses to inhibit further bradycardia pacing.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:

sensing a heart chamber designated as the rate chamber and generating sense signals upon detection of depolarization occurring in the rate chamber;

pacing a heart chamber contralateral to rate chamber, designated as the synchronized chamber, with an escape interval that is reset by either a synchronized chamber pace or a rate chamber sense;

rendering the rate chamber sensing channel refractory for a selected timing refractory period upon delivery of a synchronized chamber pace during which rate chamber senses are ignored for purposes of resetting the escape interval but counted for purposes of tachyarrhythmia detection.

2. The method of claim 1 further comprising rendering the rate chamber sensing channel refractory for a selected cross-chamber sensing refractory period upon delivery of a synchronized chamber pace during which no sensing of rate chamber events occurs, the cross-chamber sensing refractory period being shorter than the timing refractory period.

3. The method of claim 2 wherein the cross-chamber sensing refractory period is at least partially implemented by blanking a sensing amplifier of the rate chamber sensing channel.

4. The method of claim 1 wherein right and left ventricles are the rate and synchronized chambers, respectively.

5. The method of claim 1 wherein the paired atria are the rate and synchronized chambers.

6. The method of claim 1 wherein the synchronized chamber is paced in accordance with a synchronized chamber-only pacing mode.

7. The method of claim 1 wherein the timing refractory period is greater than one-half of the escape interval.

8. The method of claim 1 further comprising detecting a tachyarrhythmia by measuring intervals between successive rate chamber senses.

9. The method of claim 1 further comprising discontinuing the rate chamber timing refractory period if a tachyarrhythmia in the rate chamber is detected.

10. The method of claim 9 further comprising initiating anti-tachycardia pacing or shock therapy if a tachyarrhythmia in the rate chamber is detected.

11. A cardiac rhythm management device, comprising:

a sensing channel for sensing depolarizations from a heart chamber designated as the rate chamber;

a pacing channel for delivering paces to a heart chamber contralateral to the rate chamber, designated as the synchronized chamber;

a controller programmed to pace the synchronized chamber with an escape interval that is reset by either a synchronized chamber pace or a rate chamber sense; and, wherein the controller is programmed to detect tachyarrhythmias by measuring the intervals between rate chamber senses and to render the rate chamber sensing channel refractory for a selected timing refractory period upon delivery of a synchronized chamber pace during which rate chamber senses are ignored for purposes of resetting the escape interval but counted for purposes of tachyarrhythmia detection.

12. The device of claim 11 wherein the controller is programmed such that the rate chamber sensing channel is rendered refractory for a selected cross-chamber sensing refractory period upon delivery of a synchronized chamber pace during which no sensing of rate chamber events occurs, the cross-chamber sensing refractory period being shorter than the timing refractory period.

13. The device of claim 12 wherein the rate chamber sensing channel includes a sensing amplifier that is blanked during the cross-chamber sensing refractory period.

14. The device of claim 11 wherein the controller is programmed such that the right and left ventricles are the rate and synchronized chambers, respectively.

15. The device of claim 11 wherein the controller is programmed such that the paired atria are the rate and synchronized chambers.

16. The device of claim 11 wherein the controller is programmed such that the synchronized chamber is paced in accordance with a synchronized chamber-only pacing mode.

17. The device of claim 11 wherein the controller is programmed such that the timing refractory period is greater than one-half of the escape interval.

18. The device of claim 11 wherein the controller is programmed such that a tachyarrhythmia is detected by measuring intervals between successive rate chamber senses.

19. The device of claim 11 wherein the controller is programmed such that the rate chamber timing refractory period is discontinued if a tachyarrhythmia in the rate chamber is detected.

20. The device of claim 11 wherein the controller is programmed such that anti-tachycardia pacing or shock therapy is initiated if a tachyarrhythmia in the rate chamber is detected.

* * * * *